United States Patent [19]
Urbano et al.

[11] Patent Number: 6,004,270
[45] Date of Patent: Dec. 21, 1999

[54] ULTRASOUND SYSTEM FOR CONTRAST AGENT IMAGING AND QUANTIFICATION IN ECHOCARDIOGRAPHY USING TEMPLATE IMAGE FOR IMAGE ALIGNMENT

[75] Inventors: Joseph A. Urbano, Mt. Holly, N.J.; Christopher B. Knell, North Wales; Anthony P. Lannutti, Norristown, both of Pa.

[73] Assignee: Ecton, Inc., Ambler, Pa.

[21] Appl. No.: 09/103,973

[22] Filed: Jun. 24, 1998

[51] Int. Cl.$^6$ ........................................................ A61B 8/00
[52] U.S. Cl. ............................ 600/443; 600/440; 600/447
[58] Field of Search .................................. 600/437, 443, 600/444, 445, 447, 459, 454, 455, 461, 407; 382/124, 181, 190, 209; 128/916; 340/937

[56] References Cited

U.S. PATENT DOCUMENTS

| | | |
|---|---|---|
| 3,603,729 | 9/1971 | Sperber . |
| 4,335,427 | 6/1982 | Hunt et al. . |
| 4,337,481 | 6/1982 | Mick et al. . |
| 4,431,007 | 2/1984 | Amazeen et al. ........................ 600/440 |
| 4,444,196 | 4/1984 | Stein . |
| 4,585,008 | 4/1986 | Jarkewicz . |
| 4,729,379 | 3/1988 | Ohe . |
| 4,750,367 | 6/1988 | Bernatets . |
| 4,751,846 | 6/1988 | Dousse . |
| 4,785,818 | 11/1988 | Hardin . |
| 4,846,188 | 7/1989 | Yoshioka . |
| 4,878,115 | 10/1989 | Elion . |
| 4,887,306 | 12/1989 | Hwang et al. . |
| 4,888,694 | 12/1989 | Chesarek . |
| 5,000,182 | 3/1991 | Hinks . |
| 5,060,515 | 10/1991 | Kanda et al. . |
| 5,099,847 | 3/1992 | Powers et al. . |
| 5,103,823 | 4/1992 | Acharya et al. . |
| 5,142,558 | 8/1992 | Franciose . |
| 5,152,290 | 10/1992 | Freeland . |
| 5,181,513 | 1/1993 | Touboul et al. ........................ 600/443 |
| 5,233,993 | 8/1993 | Kawano ................................... 600/443 |
| 5,251,027 | 10/1993 | LaBeau . |
| 5,255,683 | 10/1993 | Monaghan . |
| 5,325,858 | 7/1994 | Moriizumi . |
| 5,325,859 | 7/1994 | Ishihara et al. .......................... 600/443 |
| 5,357,580 | 10/1994 | Forestieri et al. . |
| 5,425,366 | 6/1995 | Reinhardt et al. . |
| 5,456,257 | 10/1995 | Johnson et al. . |
| 5,467,770 | 11/1995 | Smith et al. . |
| 5,476,096 | 12/1995 | Olstad et al. . |
| 5,564,428 | 10/1996 | Soernmo et al. . |
| 5,595,179 | 1/1997 | Wright et al. . |
| 5,647,360 | 7/1997 | Bani-Hashemi et al. . |

*Primary Examiner*—Marvin M. Lateef
*Assistant Examiner*—Ali M. Imam
*Attorney, Agent, or Firm*—Akin, Gump, Strauss, Hauer & Feld, L.L.P.

[57] ABSTRACT

A difference image processing scheme and contrast-only difference image processing scheme is provided for imaging anatomic structures or vessels which have periodic physiological motion that define physiologic cycles. Image data is acquired using ultrasound imaging equipment. In the scheme, a template image is captured at a first time period. The template image comprises image data of a portion of the subject's body acquired at a selected time period during the physiologic cycle. The captured template image is stored. Next, a real-time image is taken at a second time period subsequent to the first time period. The real-time image includes image data of the portion of the subject's body acquired at the same selected time period during the physiologic cycle as the template image. The stored template image and the real-time image are simultaneously displayed on an image display. The simultaneously displayed images have a visually perceptible effect when the real-time image becomes closely aligned with the template image at the same selected time period during the physiologic cycle. After alignment is achieved, a difference image is calculated, stored and displayed. The difference image may be a contrast-only image if a contrast agent has been injected into the imaged region during the second time period. The template image improves the alignment process of pre-contrast and post-contrast images, or pre-event/post-event difference images.

24 Claims, 6 Drawing Sheets

ULTRASOUND SYSTEM FOR CONTRAST AGENT IMAGING AND QUANTIFICATION IN ECHOCARDIOGRAPHY USING TEMPLATE IMAGE FOR IMAGE ALIGNMENT

BACKGROUND OF THE INVENTION

Ultrasound imaging involves the display of information obtained from reflections of (echoes of) pulses of ultrasonic waves directed into the body. These echoes contain information about the underlying structure of the tissue and blood flow in vessels in the region exposed to ultrasound waves. One use of the ultrasound images is for contrast agent imaging for a heart study.

Figure 1:
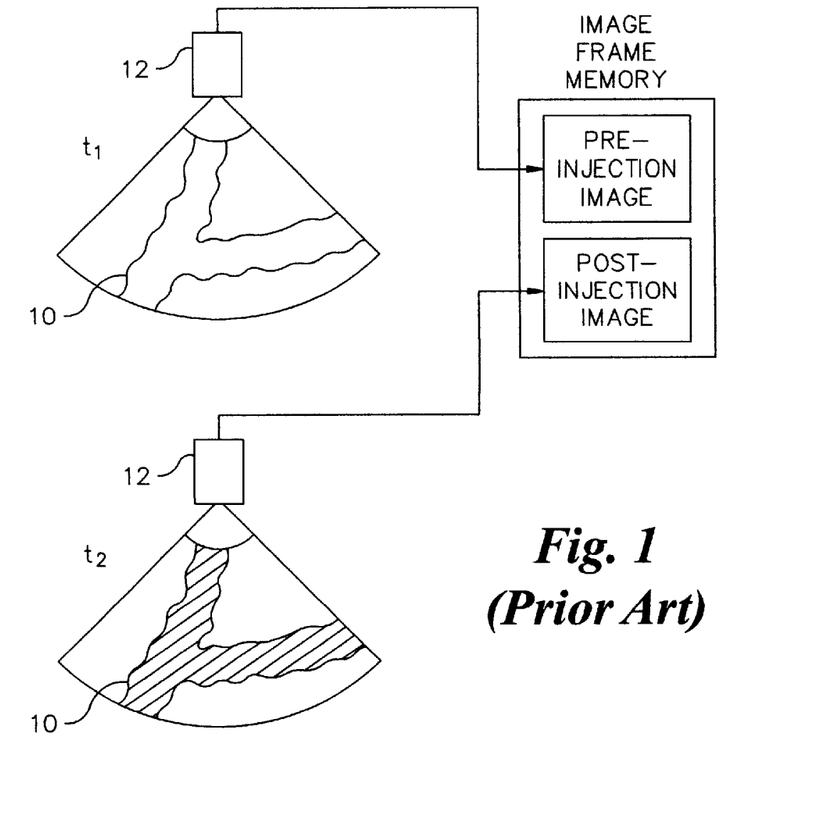
FIG. 1 illustrates the steps associated with a conventional contrast agent imaging technique for a heart study.

FIG. 1 illustrates the steps associated with a conventional contrast agent imaging technique for a heart study. First, the tissue 10 is insonated (i.e., exposed to ultrasound waves) via an ultrasound transducer probe 12 in the absence of a contrast agent, and a single image frame is acquired and stored in a first location within an image frame memory 14. The pre-injection image is acquired at a known point in the heart cycle by using a QRS trigger, such as described in U.S. Pat. No. 5,255,683 (Monaghan), incorporated in its entirety herein by reference. Next, the contrast agent is injected into the patient and another single image frame is acquired after the contrast agent has perfused into the heart vessels. This post-injection image is stored in a second location in the image frame memory 14.

Figure 2:
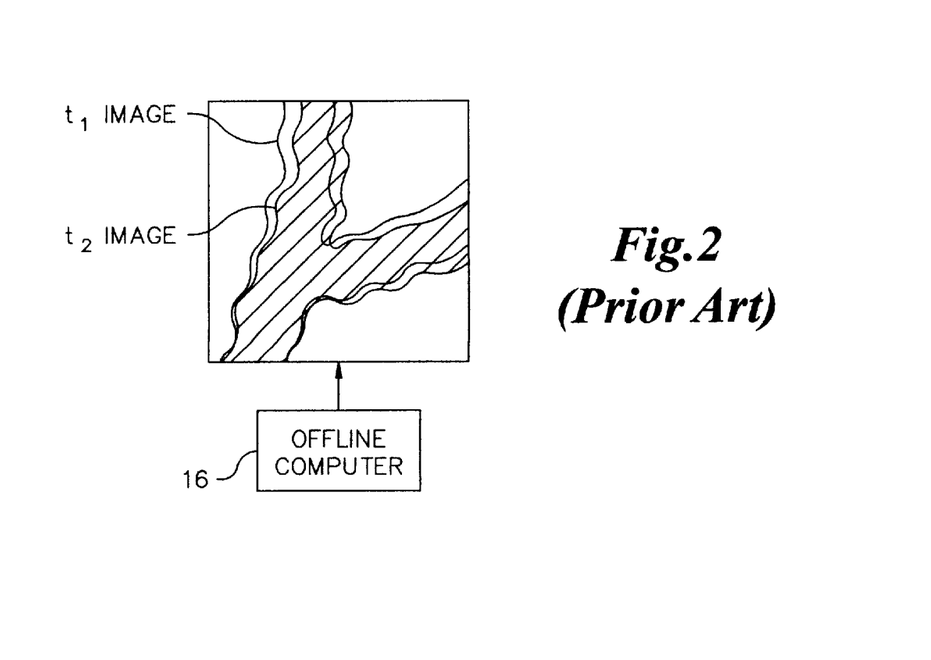
FIG. 2 illustrates a conventional offline processing scheme for use in a heart study.

Referring to FIG. 2, the two images are then processed by an offline computer 16. The computer aligns the two images as best as possible and performs a subtraction, thereby obtaining a "contrast-only difference image" (not shown). The contrast-only difference image is used for rendering a diagnosis.

To further explain the meaning of a contrast-only difference image, the subtraction of two ultrasound image frames taken at different points in time, but at the same times in the physiological cycle is referred to generically as a "difference image." A difference image is typically the absolute value of the image differences. Difference images obtained in contrast agent imaging are slightly different than generic difference images. When obtaining a contrast-only difference image of two images which are presumed to be perfectly aligned, pixel brightness differences which are less than zero are typically zeroed instead of being assigned an absolute value, since it is presumed that the post-injection image should always be brighter than the pre-injection image. That is, any pixels in the pre-contrast image which are brighter than the corresponding pixels in the post-contrast image are presumed to represent noise.

The pre-injection and post-injection images may be further improved via filtering. Filtering is useful in reducing acoustic "speckle." Acoustic speckle is caused by interference patterns from wavefronts. The interference patterns cause constructive or destructive interference. Acoustic speckle shows up as bright spots and black holes on the image. In one conventional speckle reduction technique, a plurality of pre-contrast and post-contrast images are obtained at the same point in successive cardiac cycles. Again, the QRS trigger is used as a reference point for identifying when the images should be captured. The plurality of pre-contrast and post-contrast images are then separately filtered using a conventional filtering technique, such as averaging a plurality of such images. The result is a speckle-reduced pre-contrast image and a speckle-reduced post-contrast image obtained at a single point in the cardiac cycle. The resultant filtered images are then subtracted from each other using the offline computer 16.

There are significant deficiencies in the conventional contrast agent technique. For example, there is a significant time period between acquisition of the pre-injection and post-injection image frames. In this time period, the operator may have moved the probe 12, or the patient may have moved, so that the probe 12 is not in the same exact location during the acquisition of the two images. Furthermore, it is not possible to determine that relative movement occurred during the image acquisition. The offline computer 16 can move the pre-injection image up or down, or left or right, to match up with the post-injection image. Thus, while some movement can be corrected, it is frequently impossible to exactly align the images. One reason why the images often cannot be perfectly aligned is that the images are 2-D representations of 3-D structures so that mere X-Y axis movements will not necessarily cause the images be aligned.

Figure 3A:
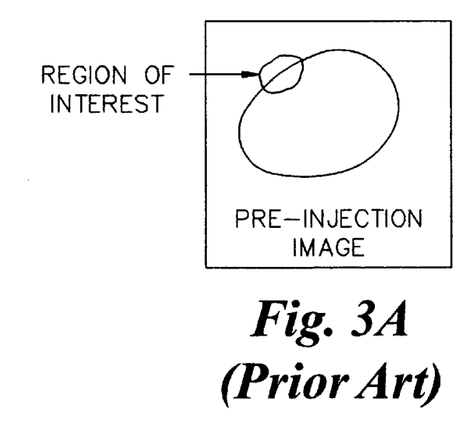
FIG. 3 illustrates display screens used for alignment processing in the conventional offline processing scheme of FIG. 2.
Figure 3B:
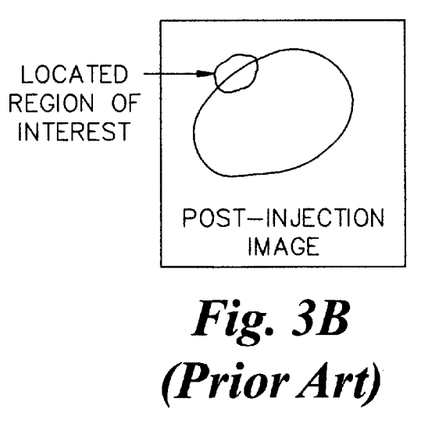
Figure 3C:
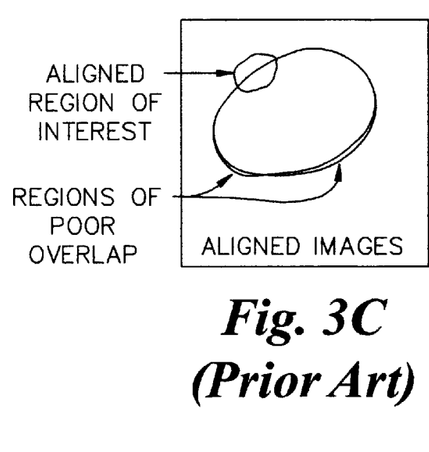

FIGS. 3A–3C show one conventional alignment scheme which uses a region-of-interest approach to automatically align the images. While the region of interest may be alignable, this does not mean that the rest of the image is necessarily aligned. See FIG. 3C which shows a perfectly overlapping region of interest, but poor overlap in other image regions. If the images cannot be accurately aligned, the resultant subtraction image will be inaccurate.

Retesting is sometimes necessary if alignment problems occur during offline processing which cannot be corrected by the computer 16. Retesting is expensive and often impractical. When the patient is suffering from an acute condition, the time lost in the process may cause a significant problem in patient management. Furthermore, the offline alignment process may introduce errors into the heart study, particularly if the operator makes a mistake in aligning the images.

At least three significant problems thus exist with the conventional technique, namely that the results are not available instantly, the patient must be retested if the images cannot be sufficiently aligned, and the offline alignment process may introduce additional errors in the heart study. Accordingly, there is a significant and unmet need for an ultrasound imaging system for contrast agent imaging which provides instant contrast images, minimizes the need for retesting, and reduces the opportunity for operator error. Furthermore, there is also a need for a difference image processing scheme which achieves such needs. The present invention fulfills all of these needs.

BRIEF SUMMARY OF THE INVENTION

Systems and methods are provided for imaging anatomic structures or vessels which have periodic physiological motion that define physiologic cycles. The systems and methods process echoes produced from transmission of ultrasound energy into a subject's body by an image frame acquisition device. A template image is captured at a first time period. The template image comprises image data of a portion of the subjects body acquired at a selected time period during the physiologic cycle. The captured template image is stored. Next, a real-time image is taken at a second time period subsequent to the first time period. The real-time image includes image data of the portion of the subject's body acquired at the same selected time period during the physiologic cycle as the template image. The stored template image and the real-time image are simultaneously displayed on an image display. The simultaneously displayed images have a visually perceptible effect when the real-time image becomes closely aligned with the template image at the same selected time period during the physiologic cycle. After alignment is achieved, a difference image is calculated, stored and displayed. The difference image may be a contrast-only image if a contrast agent has been injected into the imaged region during the second time period.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

In the drawings, like numerals are used to indicate like elements throughout.

In accordance with one preferred embodiment of the present invention, a template image is acquired prior to contrast agent injection. The template image is superimposed on the real-time image and displayed with a color map to distinguish it from the real-time image. The operator aligns the real-time image with the template image by probe manipulation just prior to and during the contrast agent injection. A contrast-only difference image is computed and captured. The contrast-only difference image may be viewed in real time or immediately after acquisition, since no post-processing or pre-contrast/post-contrast image alignment steps need to be performed. The operator can easily toggle between the contrast-only difference image and the superimposed template image and real-time image during the image acquisition session.

The image capture process may occur in a number of different ways. In one preferred embodiment of the present invention, referred to herein as the "trigger mode," the image acquisition device obtains a static template image at one point in the physiologic cycle. The static template image is frozen on the image display during acquisition of the real-time image. The real-time image may be taken during the entire physiologic cycle, or during a portion thereof. In this mode, the image display has a visually perceptible effect when the real-time, post-injection image frame display becomes closely aligned with the template image frame at the appropriate point in the physiologic cycle.

In another preferred embodiment, referred to herein as the "multiple frame mode," the image acquisition device obtains and displays a plurality of template image frames during a portion of, or during the entire physiologic cycle. The multiple frame mode thus obtains full-motion images. The sequence of template image frames are continuously replayed simultaneously with the real-time images in coordination with the physiologic cycle. In this mode, the image display has a visually perceptible effect when the real-time, post-injection image frame display becomes closely aligned with the template image frames at the same points in time in the physiologic cycle. For example, in the case of the heart cycle, a portion of the heart cycle, such as the systole portion, may be obtained for the template image, and the same portion of the heart cycle may be captured for the real-time image. The multiple frame mode requires more image processing and memory resources than the trigger mode, since the template image is composed of a plurality of image frames, instead of a single image frame. However, the multiple frame mode has an advantage over the trigger mode in that it is not necessary to wait a full physiologic cycle to see a comparison between the next real-time image and the template image. It is also easier to visually align the real-time image with the template image if the template image has a plurality of frames. In the multiple frame mode, a single contrast-only difference image may be obtained at a predesignated point in the physiologic cycle, or a plurality of contrast-only difference images may be obtained at the same portion of the physiologic cycle as the template image.

In many contrast agent heart studies, the patient's heart rate changes after injection of the contrast agent. A heart rate change will not likely cause a problem when using the trigger mode, since the image comparison occurs at only one point in the physiologic cycle. However, when using the multiple frame mode, a heart rate change may cause a mismatch in the image frames, particularly if the multiple frame mode uses the entire physiologic cycle as opposed to only a portion thereof (e.g., only the systole portion). That is, there will be a different number of template image frames in a single physiologic cycle than the number of real-time image frames in a single physiologic cycle. There are numerous solutions to this problem. One solution is to realign respective images using conventional image processing techniques, such as by using schemes described in U.S. Pat. No. 4,729,379 (Ohe) or U.S. Pat. No. 4,878,115 (Elion), both of which are incorporated by reference in their entirety herein.

Figure 4A:
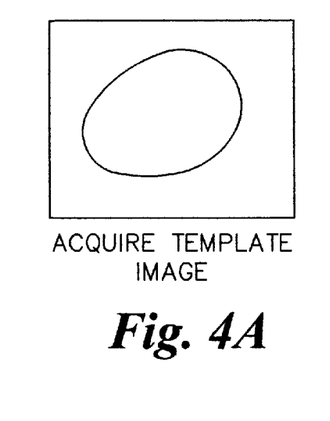
FIG. 4 illustrates an alignment processing scheme in accordance with the present invention.
Figure 4B:
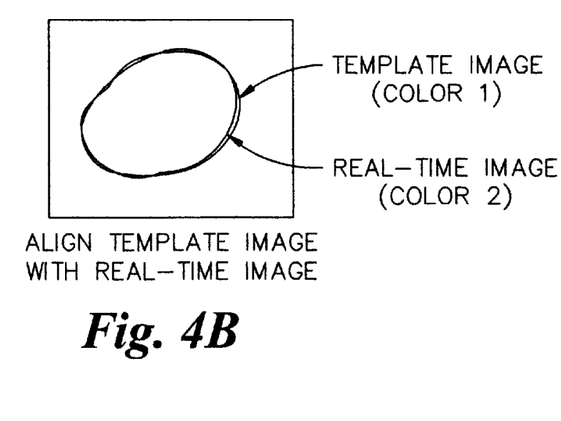

FIGS. 4A and 4B show the steps of one preferred embodiment of the present invention wherein pre-injection and post-injection images are aligned. The description of these figures include both the trigger mode and the multiple frame mode. However, to simplify the illustration of the present invention, these figures show only one template and real-time image frame. Referring to FIGS. 4A and 4B, the steps of the present invention may be summarized as follows:

(1) Capture, display and store a single image frame, or a sequence of consecutive image frames (e.g., a partial heart cycle), without the contrast agent. The image(s) may be acquired at a known point in the heart cycle by using the QRS trigger as discussed above. See FIG. 4A. This image frame (or frames) becomes the "template image."

(2) Inject the contrast agent into the patient.

(3) Align the real-time image with the still template image, or with the continuously replayed sequence of template images, after the contrast agent has entered the imaged region. See FIG. 4B. The operator performs this step by moving the probe around until the real-time image overlays the template image(s), or vice-versa.

(4) Capture and display a real-time single image frame, or a sequence of real-time consecutive image frames, after the contrast agent has entered into the heart vessels.

(5) Compute, store, and optionally view, the contrast-only difference image frame(s) at the patient site for rendering an immediate diagnosis.

As an optional step, the single image frame obtained in step (1) may be further improved via filtering during acquisition by obtaining a plurality of images at the exact same point in the cardiac cycle (using the QRS trigger as a reference point) and averaging the images, in the same manner as discussed above with respect to the prior art. Furthermore, when obtaining a plurality of template image frames and/or a plurality of real-time image frames, it is preferred to extend the prior art filtering concept to perform such filtering across the entire physiologic cycle (or the portion of the cycle being analyzed) by filtering successive image frames obtained at the same point in time within each physiologic cycle.

To assist in the alignment process of step (3), the template image or real-time image is displayed in a first color, and the other image is displayed in a second color. See FIG. 4B. As used herein, one "color" may be a grayscale (gray-scale) display wherein the strength of the ultrasound echo signal creates a visual display ranging from white for the strongest echoes to varying shades of gray. Thus, one suitable display scheme is to display the template image in grayscale, and to display the real-time image using a standard color spectrum. The scope of the invention includes any color display scheme which allows the user to visually distinguish between the template image and the real-time image.

To further assist in alignment, a low level threshold may be applied to the template image and to the real-time image to remove all pixels below a chosen intensity level. Template image pixels are displayed over real-time pixels when their intensity level is greater than the real-time image pixel intensity (i.e., when the template image shines through the real-time image). If perfect alignment is achieved, the template image would actually disappear from the screen, however, this may be difficult to achieve in practice.

The goal of the alignment step (3) above is to align tissue outlines and blood vessel outlines of the real-time image frames with the corresponding outlines in the template image frame(s). The operator sees a visually perceptible effect when alignment has occurred. Ultrasound images are characteristically made up of dark areas, typically representing blood pools or vessels, as well as bright areas representing highly reflective tissue. The arrangement of bright and dark image details describes the underlying structure of the tissue under study. Such details are especially evident when imaging the heart, which is made up of large chambers and vessels that fill with blood periodically and are surrounded by highly reflective muscle tissue. When the blood chambers are filled, they show up as dark areas of the image and the surrounding muscle tissue or "structure" is very bright. Tissue and blood vessel outlines are thus readily distinguishable as a result of the dark and bright image details.

When template images and real-time images are in alignment, the bright and dark areas of the template image overlap the bright and dark areas of the real-time image. When the images are not in alignment, the bright areas of one image cross over or cover the dark areas of the other image, and vice-versa. A visually perceptible effect occurs when the images are in alignment because the bright/dark details of the template image are closely matched to those of the real-time image and bright areas of one image do not cross over or cover dark areas of the other image.

Figure 5:
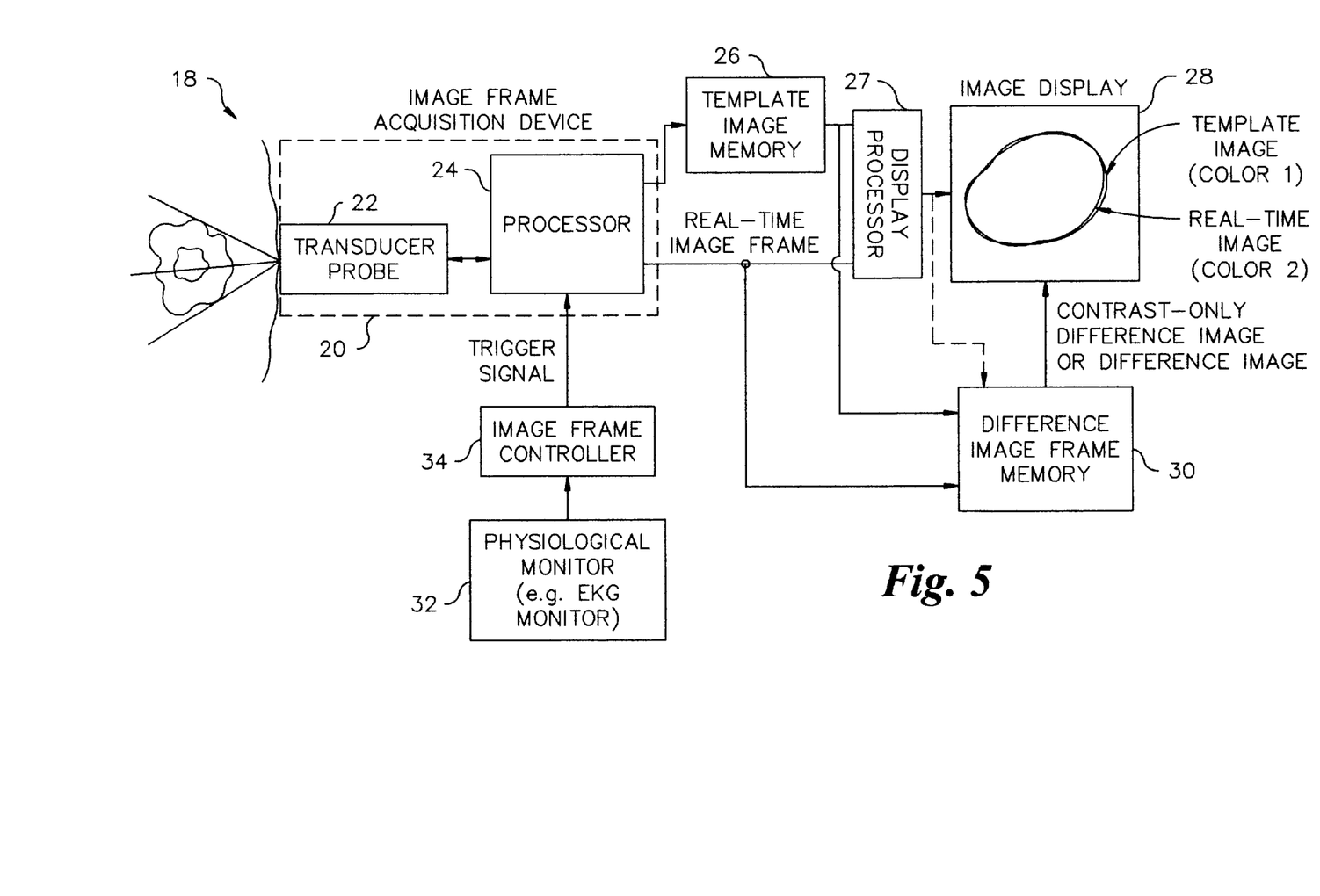
FIG. 5 is a schematic block diagram of a medical ultrasound imaging system for contrast agent imaging and difference image processing of anatomic structures which have periodic physiological motion that define physiologic cycles in accordance with the present invention.

FIG. 5 is a schematic block diagram of a medical ultrasound imaging system 18 for contrast agent imaging of anatomic structures which have periodic physiological motion that define physiologic cycles. The system 18 comprises an image frame acquisition device 20 including a transducer probe 22 and a processor 24, a template image memory 26 connected to a first output of the acquisition device 20, an image display processor 27 for receiving the output of the template image memory 26 and a second output of the processor 24, an image display 28 for receiving the output of the display processor 27, a difference image memory 30 connected at a first input to a second output of the processor 24 and connected at a second input to the output of the template image memory 26, a physiological monitor 32, and an image frame controller 34 for sending an acquisition trigger signal to the acquisition device 20 when the time of interest within the physiologic cycle is detected. The two outputs of the processor 24 schematically represent outputs at two different points in time, not necessarily two output terminals. As described below, the display processor 27 is part of the image display 28. However, these elements may be separate components of the system 18.

In the disclosed example of the present invention, the physiological monitor 32 is an EKG monitor which detects the QRS trigger, and the image frame controller 34 produces the trigger signal at a predetermined time relative to the QRS trigger.

The processor 24 processes echoes produced from transmission of ultrasound energy into a subject's body. The acquisition device 20 produces at least one template image frame prior to contrast agent injection. Each template image frame comprises data representing an image of a portion of the subject's body acquired at a given time during the physiologic cycle. The acquisition device 20 also produces real-time image frames during or after contrast agent injection. In another embodiment of the present invention, described below, the acquisition device 20 produces the real-time image frames before contrast agent injection. Each real-time image frame comprises data representing a real-time image of a portion of the subjects body acquired at the same given time during the physiologic cycle as the template image frame or frames (hereafter, "template image").

The template image memory 26 stores the template image for a given physiologic cycle.

The image display 28 simultaneously displays the stored template image and the real-time image. To assist the operator in the alignment process, the image display 28 has a visually perceptible effect when the real-time image becomes closely aligned with the template image at the same points in time of the physiologic cycle.

The difference image memory 30 stores difference image data obtained by subtraction processing of the template image and the real-time image at the same times in the physiologic cycle. If the real-time image is obtained after the contrast agent has entered the imaged region, and alignment is proper, then the difference image is a contrast-only difference image. If the real-time image is obtained without the presence of a contrast agent, and alignment is proper, and no significant anatomic or blood flow change has occurred in the imaged region since the capture time of the template image, then the difference image would theoretically be blank (i.e., all pixel values should be zero). To obtain the contrast-only image, the operator must inject the contrast agent, wait for the contrast agent to reach the region of interest, capture the real-time image, and subtract the template image therefrom. This latter scheme is described below with respect to an alternative embodiment of the present invention.

The display processor 27 causes the template image or the real-time image to be displayed in a first color, and the other image to be displayed in a second color. Optionally, the display processor 27 may apply a low level threshold to the template image, or to the template image and the real-time image, to remove all image pixels below a preset intensity level, thereby enhancing the visually perceptible effect when the real-time image becomes closely aligned with the template image at the same points in time of the physiologic cycle. If the display processor 27 further manipulates the template image stored in the template image memory 26, then the difference image memory 30 receives the template image from the output of the display processor 27 as shown in FIG. 5, instead of directly from the template image memory 26. As discussed in the background section above, when a contrast-only difference image is calculated from two aligned images, pixel brightness differences which are less than zero are zeroed instead of being assigned an absolute value.

In another preferred embodiment of the present invention, the real-time image is obtained without the presence of, or effect of, the contrast agent. In this embodiment, the real-time image is subtracted from the template image to obtain a "difference image." The real-time image may be obtained prior to contrast agent injection, preferably immediately before the contrast agent enters the vessels of interest. Alternatively, the real-time image may be obtained after contrast agent injection, but in a manner which minimizes or eliminates the effect of the contrast agent on the real-time image. For example, if a microbubble-based contrast agent is used, the microbubbles may be intentionally burst after they are detected as being in the imaged region. After being burst, the operator aligns the real-time image (now appearing without the effects of the contrast agent) with the template image. When the contrast agent returns, the contrast-only difference image is captured.

This embodiment of the present invention is generally similar to the four-step process described above, except that steps (2) and (3) are reversed.

One disadvantage of this alternative embodiment is that there is a short delay in the time between alignment of the real-time image with the template image, and the time when the contrast agent has entered the imaged region. In this delay time, the probe might move away from the aligned position. However, there is at least one significant advantage to this approach, namely that additional techniques are available to assist in image alignment which are more difficult or impossible to implement when the contrast agent is present in the real-time image.

As discussed above, when a template image and a real-time image having no contrast agent are perfectly aligned, and no significant anatomic or blood flow change has occurred in the imaged region since the capture time of the template image, the difference image should theoretically be blank (i.e., all pixel values should be zero). This may be expressed mathematically as follows:

$$\text{mean difference of pixels} = \sum_{pixels} |x(n) - t(n)| / \# \text{ of pixels}$$

wherein $x(n)$ is a real-time image frame and $t(n)$ is a template image frame. Thus, the operator has two possible visually perceptible techniques for aligning the images. First, the operator may try to overlay the two images as best as possible by using tissue and blood vessel outlines formed by bright and dark regions, as discussed above. Second, the operator may switch to a difference image mode which continuously performs the mean difference calculation above on the appropriately coordinated image frames and displays the difference image, and the operator manipulates the probe until as much of the displayed image as possible is eliminated from the image display.

Other human perceptible effects, such as an audio signal or an indicator lamp may be used in conjunction with, or as a substitute for, the image display in the alignment process. For example, an audio signal or lamp may be activated when alignment has occurred. The audio signal may have different volumes or pitches which vary depending upon how close the operator gets to the proper alignment to assist the operator in "honing in" on the correct position. The audio signal or other type of indicator may be controlled by circuitry which is responsive to the instantaneous mean difference value.

Figure 6:
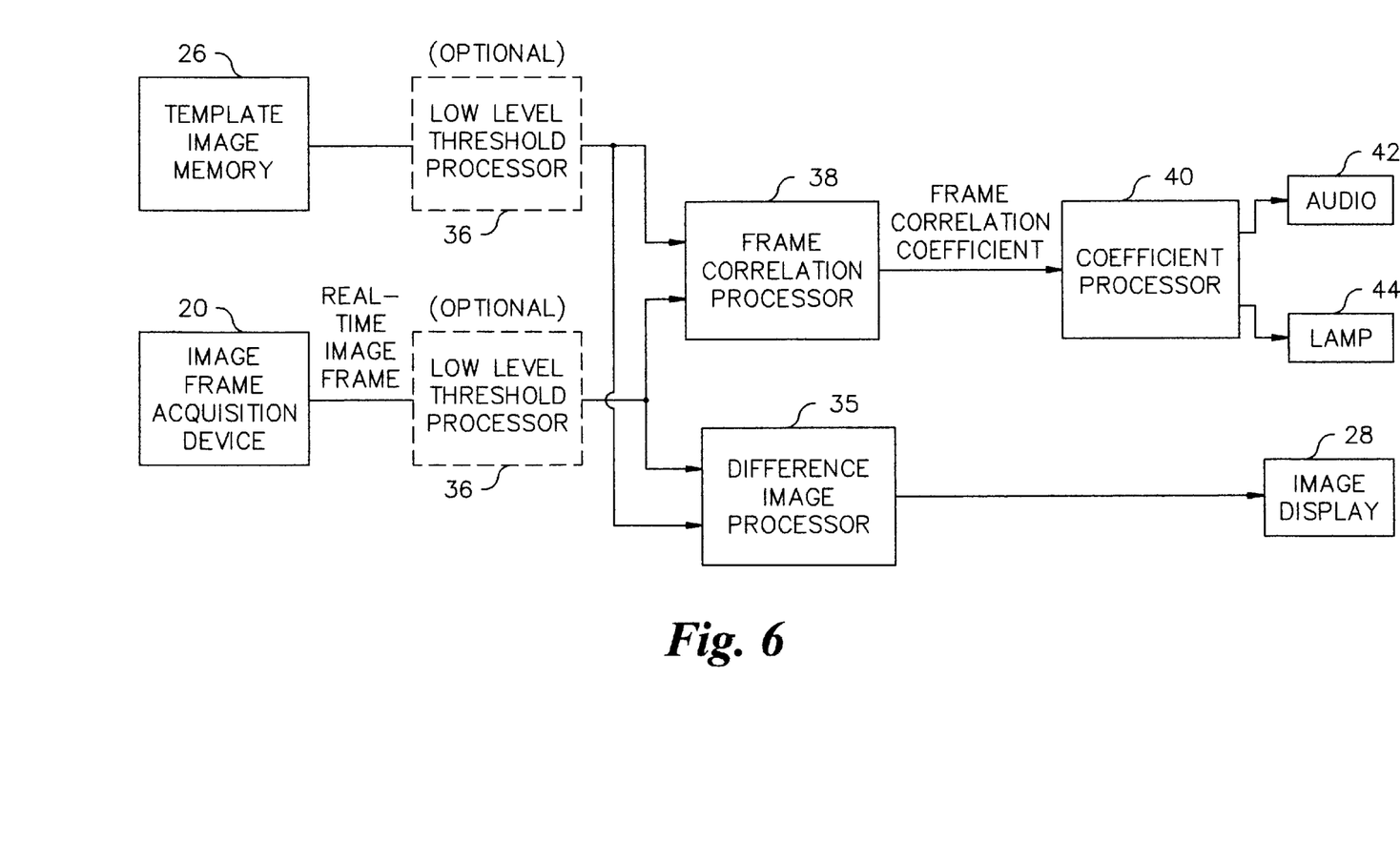
FIG. 6 is a schematic block diagram of a difference image processing system in accordance with another embodiment of the present invention.

FIG. 6 is a schematic block diagram of the elements of the system 18 for implementing such schemes. Referring to FIG. 6, the elements include the template image memory 26 and image frame acquisition device 20 of FIG. 5. The outputs of the template image memory 26 and the image frame acquisition device 20 may be processed by low level threshold processors 36 which process the image frame(s) in the same manner as the display processor 27 of FIG. 5. The raw, or processed template image and the real-time image are connected to respective inputs of a conventional frame correlation processor 34, and alternatively, to a difference image processor 35 for display on the image display 28. The display 28 may be toggled by the operator between a difference image display mode and a template image/real-time image display mode in assisting the operator during probe placement. The frame correlation processor 34 outputs a frame correlation coefficient. In a simple scheme, the frame correlation coefficient is inversely proportional to the output of the mean difference calculation discussed above. As further background to the frame correlation process, see U.S. Pat. No. 5,060,515 (Kanda et al.), incorporated in its entirety herein by reference. The output of the frame correlation processor 34 is connected to the input of a coefficient processor 40 which controls an audio device 42 and/or indicator lamp 44.

The coefficient processor 40 compares the coefficients for the image frames from the same point or points in successive physiologic cycles to locate a maximum possible value (mean difference as close as possible to zero) as the operator moves the probe 22 around the area of interest. When a maximum achievable coefficient is detected, the operator holds the probe at that location, and captures the real-time image frames at that location after the contrast agent has entered the region of interest.

In all of the embodiments discussed above, an operator input device (not shown) is provided to cause the systems of FIGS. 5 and 6 to calculate, store and/or display the difference image when the operator achieves alignment.

Storage and Packaging/formatting of Ultrasound Imaging Data for Difference Image Processing All ultrasound imaging systems have memory for collecting and storing image data. The image data may be stored as raw data representing the pixels obtained from data points along each scan line, or the image data may be stored as processed frame data, in the same manner as a frame of video. Each ultrasound system has its own data storage structure and memory structure. Accordingly, it is sometimes difficult or impossible to view image data on one ultrasound system which is acquired on a different system. Likewise, stored image data often cannot be easily shared among systems, unless the data storage structure is well understood and any necessary data conversion steps are performed. The present invention addresses these deficiencies in the prior art by providing a packaging/formatting structure for ultrasound imaging data obtained from an anatomic structure having periodic physiological motion, and which must be manipulated to perform difference image processing. The packaging/formatting structure described herein is a preferred structure for manipulating the imaging data. However, the scope of the invention also includes conventional techniques for storing ultrasound imaging data used for difference image processing.

The imaging data, in accordance with the preferred embodiment of the present invention, is stored and packaged or formatted as image loops. Each image loop includes frame data representing a plurality of image frames acquired at spaced time intervals within a single physiologic cycle. The image frames referred to herein may be template image frames acquired in the multiple frame mode, or real-time image frames.

Figure 7A:
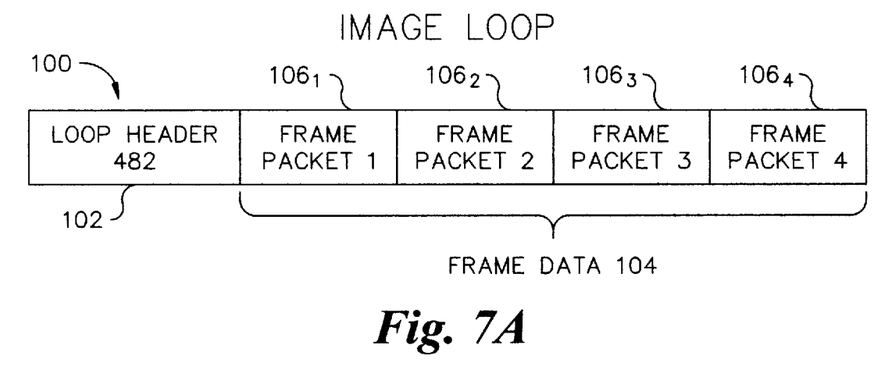
FIGS. 7A–7C show the structure of image loops for use with the present invention.

FIG. 7A shows an image loop 100. The image loop 100 includes a loop header 102 and the frame data 104 for one physiologic cycle. In the simplified example of FIG. 7A provided for illustration purposes, the frame data comprises four image frames acquired during each cycle. The image frame data 104 is packaged as a plurality of frame packets $106_1$–$106_4$, described in more detail below with respect to FIG. 7B. The loop header 102 may be used to identify the loop by number, for example, cycle number 482 in a stream of collected data.

Consider an example wherein the anatomic structure is the heart, the physiologic cycle is the heart cycle, and the image loop 100 includes a plurality of image frames acquired for one physiologic cycle at a predefined time relative to a QRS trigger. For example, the image frames may be acquired from one QRS trigger to the next, or from a few milliseconds after the QRS trigger to a few milliseconds after the next QRS trigger. If the frame rate of the acquisition equipment is 30 FPS and the heart cycle is about one second, then there will be about 30 frame packets in each image loop 100 (as opposed to the four shown in FIG. 3A).

Figure 7B:
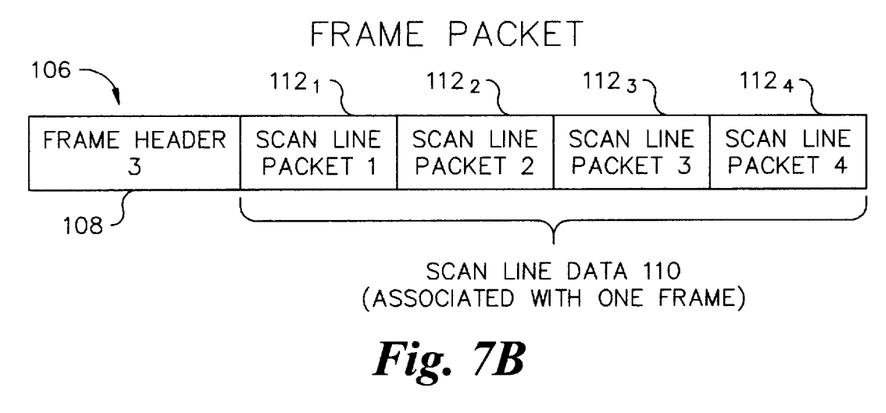

FIG. 7B shows a frame packet 106. Each frame packet 106 includes a frame header 108 and the scan line data associated with the frame. The scan line data 110 is packaged as a plurality of scan line packets $112_1$–$112_4$, described in more detail below with respect to FIG. 7C. The frame header 108 identifies the frame by number, for example, frame number 3 in the sequence of four frame packets of FIG. 7A, or frame number 3 in a sequence of 30 frame packets in the heart example described above. Alternatively, the frame numbers may begin with zero. In the heart cycle example, frame zero would be acquired at the QRS trigger or a predetermined time period displaced therefrom.

Figure 7C:
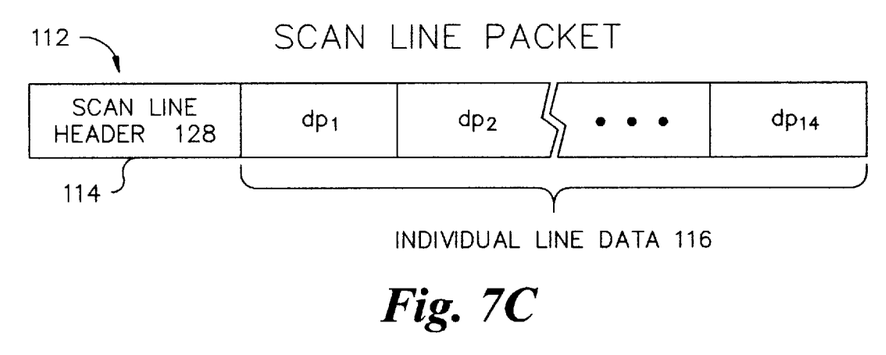

FIG. 7C shows a scan line packet 112. Each scan line packet 112 includes a scan line header 128 and the individual line data 116 associated with the scan line. The scan line header 128 comprising a line number representing a position within a scan sector, such as the last scan line shown in FIG. 1 (scan line 128). The individual line data represents the data points along a scan line.

The loop header 102, the frame header 108 and the scan line header 128 thus function much like the identification portion or ID tag of a data packet in a digital communication scheme. These headers may also be used to store additional information to assist in processing the image data. For example, the loop header 102 may also include any of the following types of information:

(1) Timing of the image loop with respect to a known point of the physiological cycle, such as the timing with respect to the QRS trigger.

(2) Time interval of the image loop. This may be used for playback control.

(3) Type of physiologic cycle (e.g., heart cycle, respiratory cycle)

(4) Geometric parameters of the ultrasound scan (e.g., apex distance, distance between the scan line data points.

(5) Number of frames or frame packets in the loop.

(6) Type of scan line data (e.g., B-mode data, color flow, harmonic mode)

The frame header 108 may also include any of the following types of information:

(1) Time between adjacent, successively acquired or collected frames (i.e., current and previous frame). This information is particularly important when image frames are acquired or collected at different frame rates. During playback, this information is used to determine how long the frame should persist on the display screen before being replaced by the next frame.

(2) Geometric parameters of the ultrasound scan, especially if one or more parameters vary on a frame-to-frame basis. If the parameters are the same for all frames, then they should be placed in the loop header to avoid redundancy of information.

(3) Number of scan lines or scan line packets in the frame packet (i.e., scan line density).

(4) Whether the image frame is a template image frame, a real-time image frame, or a difference image or contrast-only image frame. The scan line header 114 may also include any of the following types of information:

(1) Type of scan line data (2) Number of data points in the scan line or scan line packet.

(3) Number of bits per data point sample.

Additional types of information may be included in the loop, frame and scan line headers to assist in processing the image data.

One preferred embodiment of the invention for use in collecting image data of a heart cycle synchronizes frame acquisition using the QRS trigger point, wherein each image loop goes from one QRS trigger point (or a predetermined time with respect to the QRS trigger point) to the next QRS trigger point. In this manner, the real-time images which correspond with the same point in the physiologic cycle as the template image are easily identified for display processing and difference image processing by using frame header information.

Furthermore, an image loop as defined herein, starts at a first predefined time with respect to a predetermined event in a physiologic cycle and ends at a second predefined time with respect to the predetermined event in the physiologic cycle or in one or more successive physiologic cycles. In one preferred scheme, the image loop has a length of one physiologic cycle. Alternatively, the image loop may have a length greater or less than one physiologic cycle, such as one-half cycle, 1½ cycles, or two cycles. For example, an image loop may consist of only the systole portion of a heart cycle, or may consist of two full heart cycles. When the image loop has a length of one physiologic cycle, the image loop may start at the beginning of a first physiologic cycle and end at the end of the same physiologic cycle, right before the start of the next physiologic cycle. However, the image loop is not necessarily acquired from the same physiologic cycle. The image loop for the single physiologic cycle may, for example, be made up of image frames from the second half of a first physiologic cycle and the first half of the subsequent physiologic cycle. The frames in the image loop are still ordered from the start of the physiologic cycle to the end of the physiologic cycle, as determined by the collection time of the image frame with respect to the triggering event.

Consider a simplified example of four physiologic cycles, A, B, C and D, wherein four image frames 1–4 are taken per cycle. The time sequence of image cycles would be as follows:

A1 A2 A3 A4 B1 B2 B3 B4 C1 C2 C3 C4 D1 D2 D3 D4

The first three image loops may be packaged by the single cycles, as follows:

Image loop 1—A1 A2 A3 A4

Image loop 2—B1 B2 B3 B4

Image loop 3—C1 C2 C3 C4

Alternatively, if data capturing/storage does not begin until the middle of the first physiologic cycle, the image loops may be packaged as follows:

Image loop 1—B1 B2 A3 A4

Image loop 2—C1 C2 B3 B4

Image loop 3—D1 D2 C3 C4

Since image data is presumed to be relatively similar from cycle to cycle, there should theoretically be very little difference between the respective image loops in the single cycle packaging scheme vs. the adjacent cycle packaging scheme, assuming that no sudden events are occurring in the imaged anatomic structure.

Figure 8:
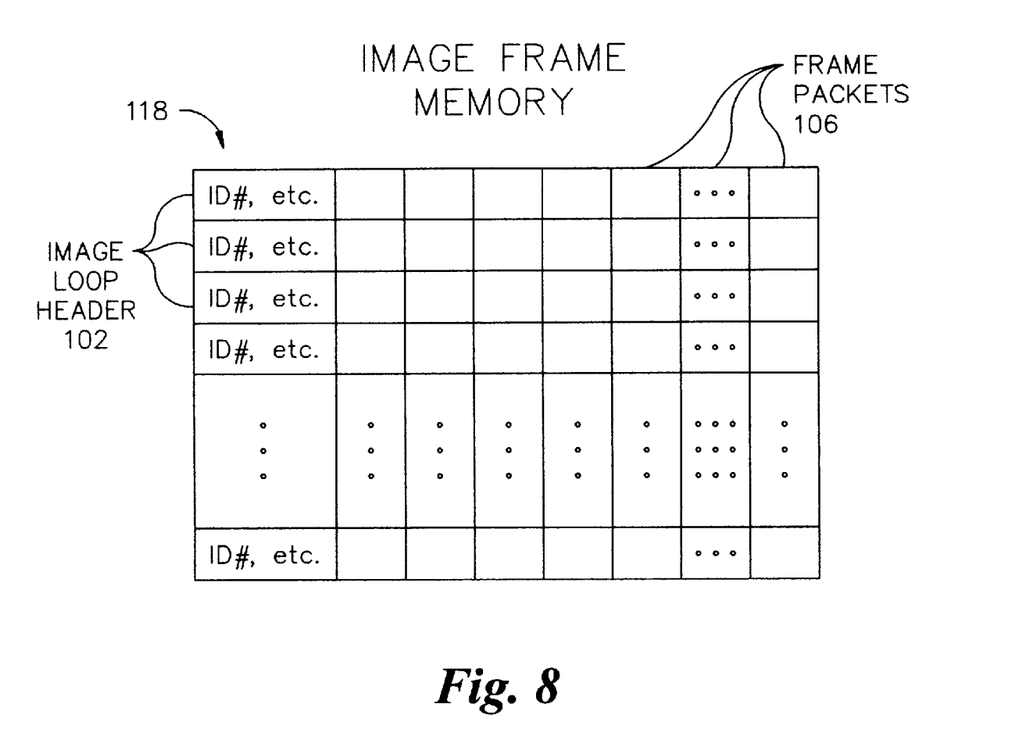
FIG. 8 is an image frame memory for storing ultrasound image frame data as a series of image loops shown in FIGS. 7A–7C.

FIG. 8 is an image frame memory 118 for storing ultrasound image frame data as a series of image loops 100. Each image loop 100 includes an image loop header 102 and a plurality of frame packet 106.

By packaging the image data in image loops, the image data becomes very easy to manipulate by the memory and processing elements of FIGS. 5 and 6. Disparate equipment can easily interpret the image data for display. Image loops simplify memory management of the image data because selected portions of data can be easily identified for storage, retrieval or display.

Although the present invention is described in the context of a heart contrast study, the scope of the invention includes other applications wherein contrast agent image studies are performed on other types of anatomic structures which have periodic physiological motion that define physiologic cycles. The scope of the invention also includes other applications where imaging is performed at different times with or without contrast imaging and where alignment and difference image processing using template image(s) may be valuable. Examples of such applications include stress echocardiography and serial imaging studies which evaluate the effect of therapeutic intervention. In these examples, the mean difference values will not necessarily approach zero, since there may be significant anatomic or blood flow changes in the imaged region subsequent to acquisition of the template image.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A medical ultrasound imaging system for imaging anatomic structures or vessels which have periodic physiological motion that define physiologic cycles, the system comprising:

(a) an image frame acquisition device having a processor for processing echoes produced from transmission of ultrasound energy into a subject's body, the acquisition device producing (i) a template image taken at a first time period, the template image comprising image data of a portion of the subject's body acquired at a selected time period during the physiologic cycle, and (ii) a real-time image taken at a second time period subsequent to the first time period, the real-time image including image data of the portion of the subject's body acquired at the same selected time period during the physiologic cycle as the template image;

(b) a template image memory for storing the template image; and (c) an image display connected to the template image memory and the image frame acquisition device for simultaneously displaying the stored template image and the real-time image, the image display having a visually perceptible effect when the real-time image becomes closely aligned with the template image at the same selected time period during the physiologic cycle.

2. A system according to claim 1 wherein the image display includes an image display processor for causing the template image or the real-time image to be displayed in a first color, and other image to be displayed in a second color.

3. A system according to claim 2 wherein the image display includes an image display processor for applying a low level threshold to the template image and the real-time image.

4. A system according to claim 1 wherein the acquisition device includes an imaging probe for acquiring the template image and the real-time image.

5. A system according to claim 1 wherein the real-time image is obtained during or after injection of a contrast agent into the imaged region, the system further comprising:

(d) a difference image memory for storing difference image data obtained by subtraction processing of the template image and the real-time image at the same selected time period during the physiologic cycle.

6. A system according to claim 1 wherein the template image is a single image frame obtained at a single selected point in time during the physiologic cycle, the image display having a visually perceptible effect when the real-time image becomes closely aligned with the single template image frame at the same selected point in time during the physiologic cycle.

7. A system according to claim 1 wherein the template image is a plurality of image frames, the image display having a visually perceptible effect when the real-time image frames become closely aligned with the template image frames at the same selected time period during the physiologic cycle.

8. A system according to claim 1 wherein the template image is displayed in grayscale.

9. A system according to claim 1 wherein the template image and the real-time image are stored and manipulated as image loops.

10. A medical ultrasound imaging system for imaging anatomic structures or vessels which have periodic physiological motion that define physiologic cycles, the system comprising:

(a) an image frame acquisition device having a processor for processing echoes produced from transmission of ultrasound energy into a subject's body, the acquisition device producing (i) a template image taken at a first time period, the template image comprising data representing an image of a portion of the subject's body acquired at a selected time period during the physiologic cycle, and (ii) a real-time image at a second time period subsequent to the first time period, the real-time image comprising data representing a real-time image of a portion of the subject's body acquired at the same selected time period during the physiologic cycle as the template image;

(b) a template image memory for storing the template image; and (c) a difference image processor connected to the template image memory and the image frame acquisition device for obtaining a difference image of the template image and the real-time image at the same selected time period during the physiologic cycle; and (d) an image display connected to the difference image processor for displaying the difference image, the difference image having a visually perceptible effect when the real-time image becomes closely aligned with the template image at the same selected time period during the physiologic cycle.

11. A medical ultrasound imaging system for imaging anatomic structures or vessels which have periodic physiological motion that define physiologic cycles, the system comprising:

(a) an image frame acquisition device having a processor for processing echoes produced from transmission of ultrasound energy into a subject's body, the acquisition device producing (i) a template image taken at a first time period, the template image comprising data representing an image of a portion of the subject's body acquired at a selected time period during the physiologic cycle, and (ii) a real-time image at a second time period subsequent to the first time period, the real-time image comprising data representing a real-time image of a portion of the subject's body acquired at the same selected time period during the physiologic cycle as the template image;

(b) a template image memory for storing the template image; and (c) a frame correlation processor connected to the template image memory and the image frame acquisition device for obtaining and outputting a frame correlation coefficient of the template image and the real-time image at the same selected time period during the physiologic cycle; and (d) human perceptible means connected to the output of the frame correlation processor for indicating the degree of correlation of the template image and the real-time image at the same selected time period during the physiologic cycle.

12. A method of imaging anatomic structures or vessels which have periodic physiological motion that define physiologic cycles by processing echoes produced from transmission of ultrasound energy into a subject's body by an image frame acquisition device, the method comprising:

(a) capturing a template image at a first time period, the template image comprising image data of a portion of the subject's body acquired at a selected time period during the physiologic cycle, (b) storing the captured template image;

(c) capturing a real-time image at a second time period subsequent to the first time period, the real-time image including image data of the portion of the subject's body acquired at the same selected time period during the physiologic cycle as the template image; and (d) simultaneously displaying the stored template image and the real-time image on an image display, the simultaneously displayed images having a visually perceptible effect when the real-time image becomes closely aligned with the template image at the same selected time period during the physiologic cycle.

13. A method according to claim 12 wherein the acquisition device includes an imaging probe for acquiring the template image and the real-time image, the method further comprising:

(e) aligning the real-time image with the template image by manipulating the location of the probe while viewing the simultaneous display generated in step (d).

14. A method according to claim 13 further comprising:

(e) obtaining a difference image by performing subtraction processing of the template image and the real-time image at the same selected time period during the physiologic cycle when alignment is achieved; and (f) storing the difference image.

15. A method according to claim 14 further comprising injecting a contrast agent into the imaged region between steps (b) and (c), the alignment step (e) being performed after the contrast agent has entered the imaged region, the difference image representing a contrast-only difference image.

16. A method according to claim 14 further comprising:

(g) viewing the difference image on the image display.

17. A method according to claim 13 further comprising injecting a contrast agent into the imaged region between steps (b) and (c), the alignment step (e) being performed after the contrast agent has entered the imaged region.

18. A method according to claim 12 wherein step (d) includes displaying the template image or the real-time image in a first color, and displaying the other image in a second color.

19. A method according to claim 18 further comprising the step of applying a low level threshold to the template image and the real-time image.

20. A method according to claim 12 further comprising after step (b), injecting a contrast agent into the imaged region.

21. A method according to claim 12 wherein the template image captured in step (a) is a single image frame obtained at a single selected point in time during the physiologic cycle, the image display having a visually perceptible effect when the real-time image becomes closely aligned with the single template image frame at the same selected point in time during the physiologic cycle.

22. A method according to claim 12 wherein the template image captured in step (a) is a plurality of image frames, the image display having a visually perceptible effect when the real-time image frames become closely aligned with the template image frames at the same selected time period during the physiologic cycle.

23. A method according to claim 12 wherein the template image is displayed in grayscale.

24. A method according to claim 12 further comprising the step of storing and manipulating the template image and the real-time image as image loops.

* * * * *